(12) United States Patent
Bae et al.

(10) Patent No.: US 8,367,023 B2
(45) Date of Patent: Feb. 5, 2013

(54) REAGENT VESSEL (75) Inventors: Byeong-woo Bae, Anyang-si (KR);
Sung-dong Lee, Anyang-si (KR);
Min-sun Kim, Anyang-si (KR);
Jae-hyun Yoo, Anyang-si (KR);
Hyoung-soo Kim, Anyang-si (KR);
Heon-seok Park, Anyang-si (KR);
Ju-pyo Hong, Anyang-si (KR)

(73) Assignee: Infopia Co., Ltd., Anyang-Si (KR)

( * ) Notice: Subject to any disclaimer, the term of this patent is extended or adjusted under 35 U.S.C. 154(b) by 275 days.

(21) Appl. No.: 12/602,082

(22) PCT Filed: Jun. 24, 2008

(86) PCT No.: PCT/KR2008/003588
§ 371 (c)(1),
(2), (4) Date: Nov. 25, 2009

(87) PCT Pub. No.: WO2009/061054
PCT Pub. Date: May 14, 2009

(65) Prior Publication Data
US 2010/0196999 A1 Aug. 5, 2010

(30) Foreign Application Priority Data
Nov. 8, 2007 (KR) .......................... 10-2007-0113899

(51) Int. Cl.
*G01N 15/06* (2006.01)
*G01N 33/00* (2006.01)
*G01N 33/48* (2006.01)

(52) U.S. Cl. ......... 422/550; 422/50; 422/68.1; 422/554; 422/560; 422/561; 436/43

(58) Field of Classification Search .................... 436/43; 422/68.1, 550, 50, 554, 560, 561
See application file for complete search history.

(56) References Cited

U.S. PATENT DOCUMENTS
4,265,372 A * 5/1981 Wainberg .................... 222/82
(Continued)

FOREIGN PATENT DOCUMENTS
CN 1551803 A 12/2004
CN 1925916 A 3/2007
(Continued)

OTHER PUBLICATIONS
Limin Liu et al., Direct Enzymatic Assay for %HbA1c in Human Whole Blood Samples, Diazyme Laboratories, Clinical Biochemistry 41 (2008), Elsevier Inc., Poway, CA, pp. 576-583.
(Continued)

*Primary Examiner* — Brian J Sines
(74) *Attorney, Agent, or Firm* — NSIP Law (57) ABSTRACT

Provided is a reagent vessel which is inserted into a measuring cassette for measuring a biological sample. The reagent vessel includes: a reagent storage unit including at least one space in which a reagent that is to react with the biological sample is stored; and an adhesive cover sealing up the at least one space in which the reagent is stored, and being stripped off to discharge the reagent from the at least one space when the reagent vessel is inserted into the measuring cassette. Therefore, since a plurality of reagents are poured simultaneously and automatically into a measuring cassette through a reagent vessel, it is possible to simplify manipulations and minimize a measuring time. Furthermore, it is possible to resolve problems regarding storage and distribution of reagents.

10 Claims, 5 Drawing Sheets

U.S. PATENT DOCUMENTS

| | | | |
|---|---|---|---|
| 4,909,478 A * | 3/1990 | Steer | 251/352 |
| 5,120,504 A * | 6/1992 | Petro-Roy et al. | 435/287.2 |
| 5,162,237 A | 11/1992 | Messenger et al. | |
| 2004/0197233 A1 | 10/2004 | Nagaoka et al. | |
| 2006/0065565 A1 * | 3/2006 | Masuda et al. | 206/459.1 |
| 2007/0104395 A1 * | 5/2007 | Kinigakis et al. | 383/61.1 |
| 2009/0166363 A1 * | 7/2009 | Balteau | 220/523 |

FOREIGN PATENT DOCUMENTS

| | | |
|---|---|---|
| EP | 1 203 959 A1 | 5/2002 |
| JP | 03-046566 A | 2/1991 |
| JP | 04-223267 | 8/1992 |
| JP | 2004-309145 A | 11/2004 |
| JP | 2005-130851 A | 5/2005 |
| KR | 1020010031996 | 4/2001 |
| KR | 1020070001988 | 1/2007 |
| WO | WO 01/13127 A1 | 2/2001 |
| WO | WO 03/022441 A1 | 3/2003 |
| WO | WO 2005/049207 A1 | 6/2005 |

OTHER PUBLICATIONS

Lynn Bry et al., Effects of Hemoglobin Variants and Chemically Modified Derivatives on Assays for Glycohemoglobin, Clinical Chemistry 47:2 (2001), Boston, MA, pp. 153-163.

* cited by examiner

REAGENT VESSEL

TECHNICAL FIELD

The present invention relates to a reagent vessel, and more particularly, to a reagent vessel which is inserted into a reaction cassette for measuring biological samples.

BACKGROUND ART

Concentration measurement of analytes is useful in medical or environmental fields, such as medical diagnosis, medical treatment through medicine, and detection of harmful chemical materials. Concentration measurement of biological samples is of importance because the results of the measurement are used for medical diagnosis and treatment of various diseases. Such concentration measurement is executed in various places including clinical laboratories, hospitals, and home. For example, concentration measurement of glycated hemoglobin (HbA1c) in blood is useful for diagnosis and treatment of diabetes.

In order to measure analytes of biological samples, a series of chemical processes, such as reaction, stirring, or washing, using a reagent which is specifically combined with the analytes can be performed. Here, the reagent which is combined with the analytes that are to be measured may be included in a measuring apparatus or in a separate vessel. However, in the case where a reagent that is to be combined with analytes is contained and stored in a measuring apparatus, there are difficulties in keeping the reagent without any spoilage for a long time.

Meanwhile, in the case where a reagent that is to be combined with analytes is supplied through a separate reagent vessel, a vessel in which the reagent is contained may be made of glass or thermoplastics. If a vessel in which the reagent is contained is a glass bottle, a process of detecting any crack of the glass bottle is required for precise measurement of analytes because such a glass bottle is relatively expensive and breaks easily. However, since thermoplastics are lighter in weight and lower in price than glass, most of vessels for storing reagents are made of thermoplastics.

In the case where a reagent that is to react with biological samples is supplied to a measuring apparatus through a separate vessel, the vessel stores the reagent. For example, in order to measure the concentration of glycated hemoglobin in blood, a reagent vessel can store materials that specifically react with glycated hemoglobin.

However, in this case, separate reagent vessels for storing respective reagents that are to be specifically combined with glycated hemoglobin in blood are needed. Also, a measurer should pour reagents contained in a plurality of reagent vessels into a measuring apparatus at regular time intervals. Particularly, in the case where the plurality of reagent vessels are vacuum tubes, operation of opening the vacuum tubes and then pouring reagents contained in the vacuum tubes into the measuring apparatus is needed. However, since the operation requires the direct intervention of a measurer, the measure will feel inconvenient. Also, such manipulations may make a measuring process difficult, which inevitably delays a measuring time.

DISCLOSURE OF INVENTION

Technical Problem

Accordingly, the present invention provides a reagent vessel which can move at least one reagent automatically to a measuring cassette for measuring biological samples only by inserting the reagent vessel into the measuring cassette, thereby simplifying manipulations. Therefore, since reagents are supplied to the measuring cassette through the reagent vessel, it is possible to resolve problems regarding storage and distribution of reagents.

Technical Solution

In order to achieve the object, the prevent invention provides a reagent vessel which can simultaneously and automatically transfer at least one reagent to a measuring cassette for measuring biological samples by inserting the reagent vessel into the measuring cassette.

According to an aspect of the present invention, there is provided a reagent vessel which is inserted into a measuring cassette for measuring a biological sample, the reagent vessel including: a reagent storage unit including at least one space in which a reagent that is to react with the biological sample is stored; and an adhesive cover sealing up the at least one space in which the reagent is stored, and being stripped off to discharge the reagent from the at least one space when the reagent vessel is inserted into the measuring cassette.

The reagent vessel further includes a tap part formed in an edge of the reagent storage unit, and cut off by the measuring cassette when the reagent vessel is inserted into the measuring cassette, and further includes a tap projection formed on the tap part, and a catching slot in which the tap projection is caught when the tap part is folded.

Also, the reagent vessel further includes a sample injecting unit in which biological samples, such as blood or urine, are injected, and a storage space for storing biological samples can be partitioned into a plurality of storage spaces so that different biological reagents are stored separately in different storage spaces.

Advantageous Effects

As described above, since a reagent vessel according to the present invention can simultaneously and automatically pour a plurality of reagents into a measuring cassette, it is possible to simplify manipulations and minimize a measuring time.

That is, since at least one reagent simultaneously inflows to a measuring cassette only by inserting a reagent vessel in which the at least one reagent is stored into the measuring cassette, easy manipulation is possible and a measuring time can be reduced. Also, since an adhesive cover is automatically stripped off to move the reagent to the measuring cassette when the reagent vessel is inserted into the measuring cassette, manipulations can be simplified. Accordingly, a measurer needs not to sequentially pour a plurality of reagents that are to react with biological samples, into the measuring cassette, at regular time intervals, in order to measure the concentration of the biological samples.

Also, since reagents are stored in a separate reagent vessel without being stored in a measuring cassette, problems regarding storage or distribution of reagents can be solved and spoilage of reagents can be prevented. Also, since reagents are stored in a separate reagent vessel, the size of a measuring cassette can be minimized. Furthermore, it is possible to pour a correct amount of reagent into a measuring cassette for quantitative analysis of biological samples.

Meanwhile, by additionally installing a sample injecting unit in the reagent vessel, the reagent vessel can have an integrated structure in which a sample injecting unit and a reagent storage space exist together. Accordingly, at least one reagent and biological samples are simultaneously transferred to a measuring cassette so that the at least one reagent and biological samples react with each other in the measuring cassette.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

MODE FOR THE INVENTION

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art.

Figure 1:
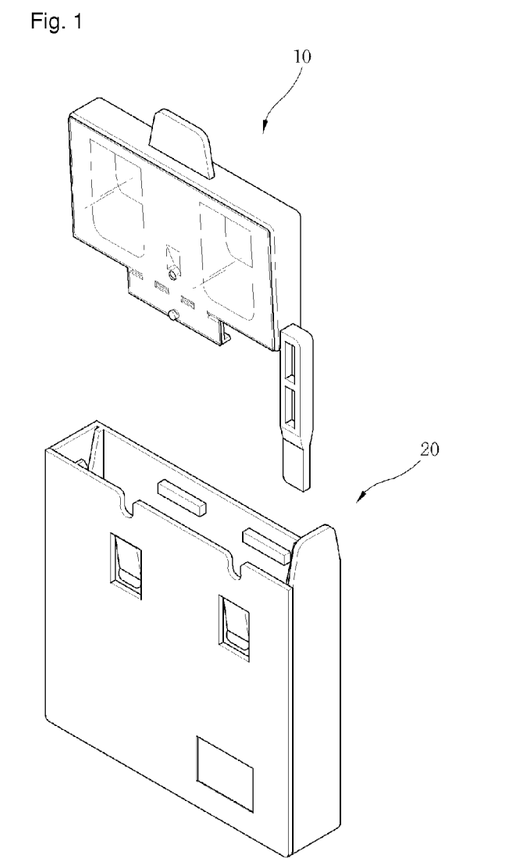
FIG. 1 is a perspective view showing a measuring cassette and a reagent vessel according to an embodiment of the present invention.

FIG. 1 is a perspective view showing a measuring cassette 20 and a reagent vessel 10 according to an embodiment of the present invention.

Referring to FIG. 1, the measuring cassette 20 is used to measure liquid biological samples. The liquid biological samples are test samples which are obtained from human bodies. For example, the biological samples are human body secretions, such as blood, urine, plasma, serum, cerebral liquid, spinal liquid, or saliva. However, the biological samples are not limited to the above-mentioned human body secretions.

The measuring cassette 20 can be used to measure the concentration of glycated hemoglobin in blood. Glycated hemoglobin, which is a type of hemoglobin, exists in red blood cells in blood. When the concentration of blood sugar (glucose) in blood is high, a part of the glucose in the blood is combined with hemoglobin. The hemoglobin combined with the glucose is called glycated hemoglobin, or HbA1c. Blood sugar levels can be determined by measuring the concentration of glycated hemoglobin in the blood. The measurement of glycated hemoglobin in the blood can be conducted regardless of mealtime.

The reagent vessel 10 is used to store a reagent that is to react with liquid biological samples so that the measuring cassette 20 can measure the liquid biological samples. Here, the reagent vessel 10 may be made of plastics. Details for the reagent vessel 10 will be described later with reference to the drawings.

Meanwhile, the measuring cassette 20 receives a reagent and/or sample from the reagent vessel 10, and can perform quantitative analysis on a mixture of the reagent and/or sample.

In detail, the measuring cassette 20 can receive at least one reagent from the reagent vessel 10. For example, when the concentration of glycated hemoglobin in a blood sample is measured through the measuring cassette 20, the measuring cassette 20 can receive at least one reagent from the reagent vessel 10. At this time, the concentration of glycated hemoglobin can be measured from a mixture of the blood sample and the reagent.

Also, the measuring cassette 20 may measure the concentration of microalbumine/creatinine in urine, in this manner, as well as measure the concentration of glycated hemoglobin in blood. At this time, through quantitative analysis of microalbumine/creatinine, medical diagnosis and treatment of complications caused by diabetes are possible. However, the biological samples that are to be measured are not limited to glycated hemoglobin or microalbumine/creatinine, and various biological samples can be measured by the measuring cassette 29.

FIGS. 2 through 5 are views showing the reagent vessel 10 at different view angles.

Figure 2:
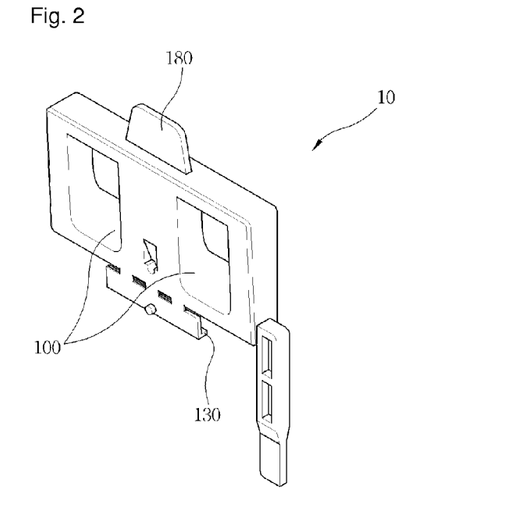
FIG. 2 is a perspective view of a reagent vessel according to an embodiment of the present invention.
Figure 3:
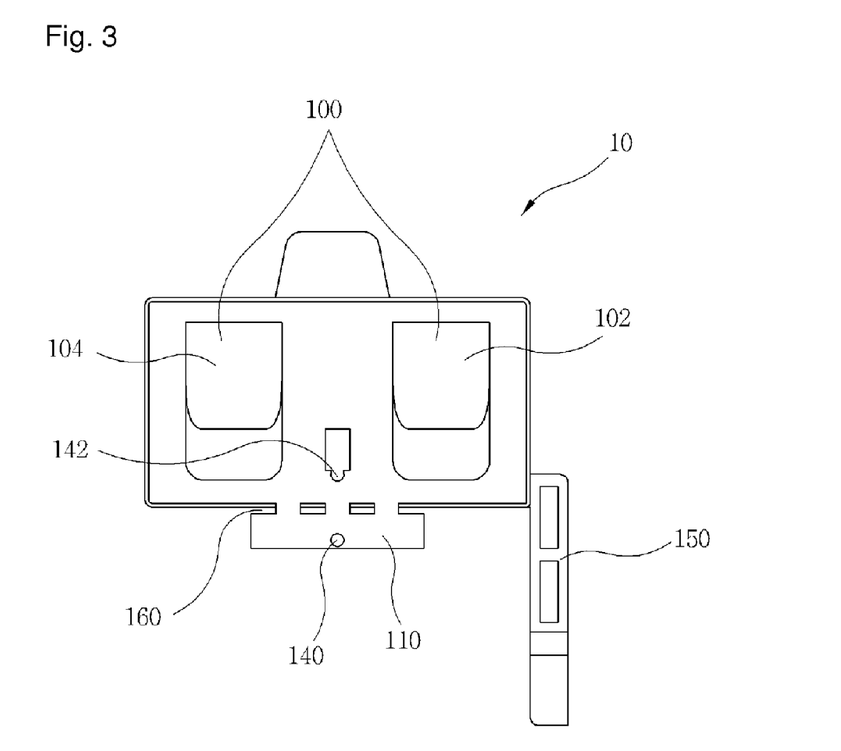
FIG. 3 is a cross-sectional view of the reagent vessel illustrated in FIG. 2.

FIG. 2 is a perspective view of the reagent vessel 10, and FIG. 3 is a cross-sectional view of the reagent vessel 10.

Figure 5:
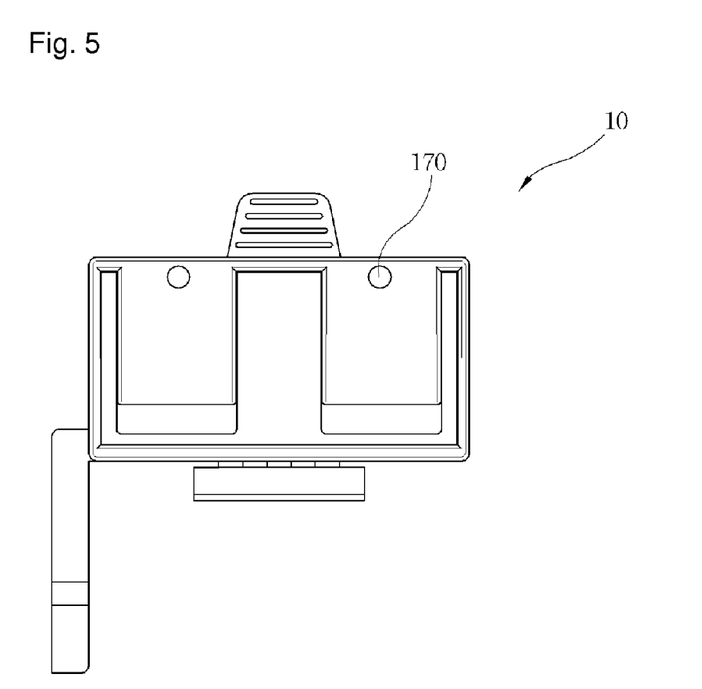
FIG. 5 is a rear view of the reagent vessel illustrated in FIG. 2.
Figure 6:
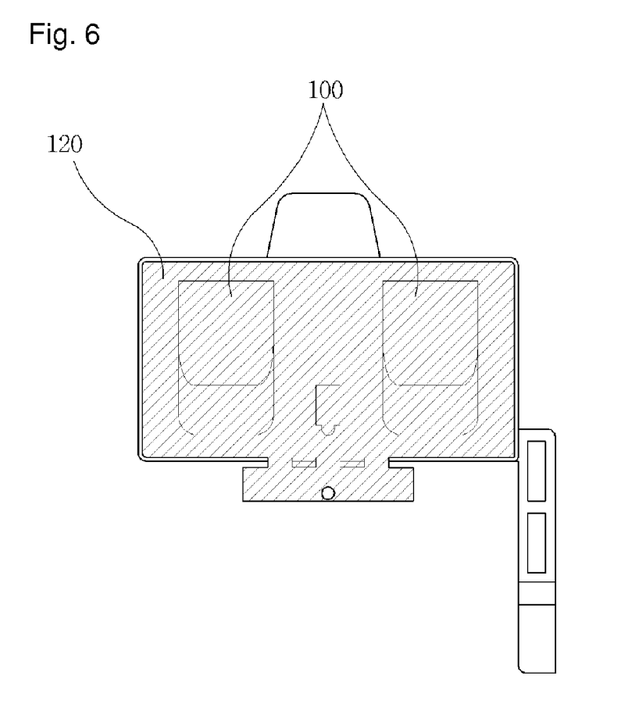
FIG. 6 shows an adhesive cover of the reagent vessel illustrated in FIG. 2.

Referring to FIGS. 2 and 3, the reagent vessel 10 includes a reagent storage unit 100 and an adhesive cover (120 in FIG. 6). Also, the reagent vessel 10 can further include a tap part 110, a catching member 130, a tap projection 140, a sample injecting unit 150, a cutting unit 160, a cassette catching projection (170 in FIG. 5), and a handle 180.

Here, the reagent storage unit 100 includes one or more storage spaces in which reagents are stored. The adhesive cover 120 seals up the storage spaces included in the reagent storage unit 100 so that the reagents do not flow out of the storage spaces. When the reagent vessel 10 is inserted into the measuring cassette 20, the adhesive cover 120 is stripped off by the tap part 110 to discharge the reagents therein into the measuring cassette 20.

Hereinafter, the construction of the reagent vessel 10 will be described in detail.

The reagent storage unit 100 includes one or more spaces in which reagents are stored. That is, the reagent storage unit 100 may include a single space in which a reagent is stored, or may include a plurality of spaces in which a plurality of reagents are stored. For example, as illustrated in FIG. 2, the reagent storage unit 100 includes first and second spaces 102 and 104 in order to measure the concentration of glycated hemoglobin in a blood sample.

Hereinafter, a reagent which can be stored in the reagent storage unit 100 to measure the concentration of glycated hemoglobin in a blood sample will be described in detail.

When the concentration of glycated hemoglobin is measured, the first space 102 of the reagent storage unit 100 stores a first reagent. A blood sample reacts with the first reagent poured through the reagent vessel 10 in the measuring cassette 20, and then a total amount of hemoglobin is measured from a blood sample mixture which has reacted with the first reagent. The first reagent may be glycated hemoglobin binding material-beads which combine specifically with glycated hemoglobin and hemolysate which hemolyzes a blood sample.

In detail, the hemolysate is a buffer solution containing a surface active agent. For example, the hemolysate is N-2-Hydroxyethylpiperazine-N'-2-ethanesulfonic Acid HEPES; PH 8.1. The glycated hemoglobin binding material is a material which can combine specifically with glycated hemoglobin, for example, the glycated hemoglobin-binding material is one of boronic acid (BA), concanavalin A (Lectin), and antibody. The beads may be polymer polysaccharide support (such as agarose, cellulose, or sepharose), latex beads (such as polystyrene, polymethylmethacrylate, or polyvinyltolune), or glass beads.

Meanwhile, the second space 104 of the reagent storage unit 100 stores a second reagent. The second reagent may include a washing solution for washing off the blood sample mixture.

Most of hemoglobin (Hb) existing in red blood cells of a blood sample is non-glycated hemoglobin (Ao). Only 4.0-14.0% of the non-glycated hemoglobin reacts with glucose, and becomes glycated hemoglobin (HbA1c). Accordingly, the blood sample mixture which has reacted with the glycated hemoglobin binding material-beads of the first reagent includes both non-glycated hemoglobin and glycated hemoglobin. Therefore, in order to measure only the glycated hemoglobin in the blood sample, it is needed to remove the non-glycated hemoglobin from the blood sample. For this reason, the second reagent includes a washing solution for washing off the non-glycated hemoglobin from the blood sample.

As illustrated in FIG. 3, the reagent storage unit 100 can partition a space for storing reagents into two spaces of the first space 102 and the second space 104 so that the first and second reagents can be stored separately in different spaces. Accordingly, only by inserting the reagent vessel 10 into the measuring cassette 20, a plurality of reagents can be simultaneously discharged into different spaces. This is aimed to react a plurality of reagents with targets that are to be measured or detect any specific material using the plurality of reagents by discharging the plurality of reagents into different areas of the measuring cassette 20. Accordingly, a measurer needs not to pour a plurality of reagents that are to react with biological samples, into the measuring cassette 20, at regular time intervals, in order to measure the concentration of the biological samples.

The adhesive cover (120 in FIG. 6) covers the first and second spaces 102 and 104 included in the reagent storage unit 100, and stores reagents in the first and second spaces 102 and 104. In detail, the adhesive cover 120 seals up the first and second spaces 102 and 104 so that at least one reagent contained in the first and second spaces 102 and 104 does not flow out. The adhesive cover 120 may be made of a thin foil, such as a vinyl film, an aluminum foil, or a tin foil. The adhesive cover 120 can be adhered to one side of the reagent vessel 10 by an adhesive.

Also, when the reagent vessel 10 is inserted into the measuring cassette 20 (see FIG. 1), the tap part 110 is cut off, and the adhesive cover (120 in FIG. 6) is automatically stripped off when the reagent vessel 10 is completely inserted into the measuring cassette 20. Accordingly, a measurer needs not to open the reagent vessel 10 in which reagents are stored, and to pour the reagents into the measuring cassette 20.

The tap unit 110 may be folded when the reagent vessel 10 is inserted into the measuring cassette 20. When the reagent vessel 10 is completely inserted into the measuring cassette 20, the reagent vessel 10 may be cut off by the measuring cassette 20. Here, the cutting unit 160 is formed between the reagent storage unit 100 and the tap part 110, and includes a plurality of slots. Accordingly, the cutting unit 160 facilitates the folding of the tap unit 100 and cuts off the tap part 110 when the reagent vessel 10 is inserted into the measuring cassette 20.

Meanwhile, the catching member 130 causes the tap unit 110 folded when the reagent vessel 10 is inserted into the measuring cassette 20 to be caught in a reagent vessel catching jar 210 of the measuring cassette 20. Due to this structure, the tap part 110 is caught in the reagent vessel catching jar 210, and cut off when the reagent vessel 10 is inserted into the measuring cassette 20, so that the adhesive cover 120 is stripped off. Accordingly, by the folding and cutting of the tap part 110, the adhesive cover 120 is automatically stripped off and the reagents are poured into the measuring cassette 20. Therefore, the reagents can be automatically moved to the measuring cassette 20 only by inserting the reagent vessel 10 into the measuring cassette 20.

The tap projection 140 is located on the tap part 110. When the reagent vessel 10 is inserted into the measuring cassette 20, the tap projection 140 is inserted into the catching slot 142 and caught in the catching slot 142 when the catching member 130 is caught in the reagent vessel catching jar 210. Accordingly, it is possible to prevent the folded tap unit 110 from shaking.

Meanwhile, the reagent vessel 10 may include the sample injecting unit 150 through which biological samples are injected. Particularly, the inside diameter of the sample injecting unit 150 may be tapered toward the tip of the sample injecting unit 150 so that a capillary phenomenon can be generated to suck samples. Also, the sample injecting unit 150 is located below the reagent storage unit 100 so that a sample gathered by the sample injecting unit 150 can react directly with a reagent poured from the reagent vessel 10. Meanwhile, the handle 180 is used to facilitate the use of the reagent vessel 10.

Figure 4:
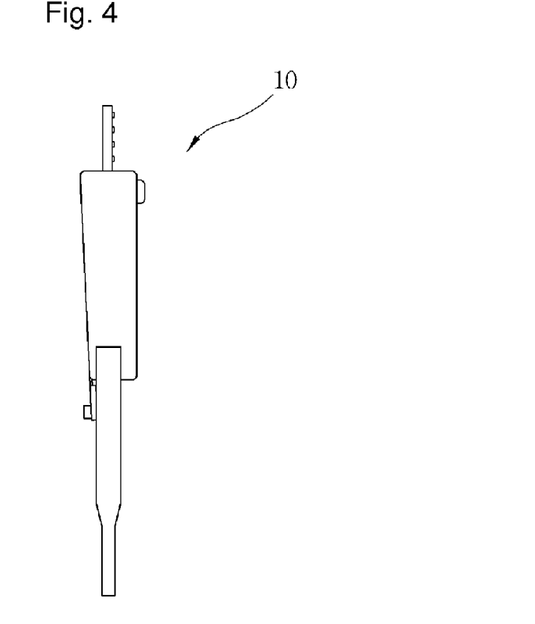
FIG. 4 is a side view of the reagent vessel illustrated in FIG. 2.

FIG. 4 is a side view of the reagent vessel 10 illustrated in FIG. 2.

Referring to FIG. 4, at least one side of the reagent vessel 10 may incline in a vertical direction. That is, at least one side of the reagent vessel 10 may incline downward in such a manner that the distance between the inclined side of the reagent vessel 10 and the corresponding wall of the measuring cassette 20 (see FIG. 1) is gradually widened downward when the reagent vessel 10 is inserted into the measuring cassette 20. Accordingly, when the reagent vessel 10 is inserted into the measuring cassette 20, a reagent contained in the reagent storage unit 100 (see FIG. 3) can flow easily into the measuring cassette 20.

Meanwhile, FIG. 5 is a rear view of the reagent vessel 10 illustrated in FIG. 2.

Referring to FIG. 5, the reagent vessel 10 may include two cassette catching projections 170 on the rear surface. The cassette catching projections 170 prevents further inserting of the reagent vessel 10 into the measuring cassette 20 when the reagent vessel 10 is completely inserted into the measuring cassette 20 so that the adhesive cover (120 in FIG. 6) is automatically stripped off and a reagent is all poured into the measuring cassette 20. Here, the cassette catching projections 170 can be caught in the measuring cassette 20 and fix the reagent vessel 10 to the measuring cassette 20.

FIG. 6 shows the adhesive cover 120 of the reagent vessel 10, according to an embodiment of the present invention.

Referring to FIG. 6, the adhesive cover 120 seals up the reagent storage units 100 of the reagent vessel 10 so that at least one reagent stored in the reagent storage unit 100 does not flow out. In order to seal up the reagent storage units 100, the adhesive cover 120 may be subjected to hot-sticking after applying an adhesive on the rear surface. By contacting the adhesive cover 120 subjected to hot-sticking to the reagent storage units 100, it is possible to prevent any reagent from leaking out of the reagent storage units 100.

Figure 7:
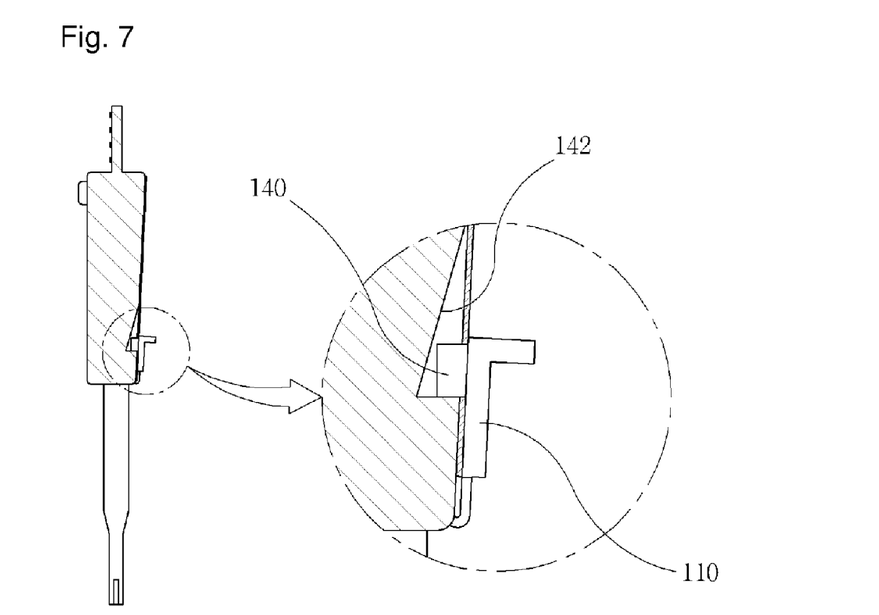
FIG. 7 is a view for explaining a state when the reagent vessel illustrated in FIG. 2 is folded.

FIG. 7 is a view for explaining a state when the reagent vessel 10 illustrated in FIG. 2 is folded.

Referring to FIG. 7, the reagent vessel 10 includes a tap projection 140 and a catching slot 142. The tap projection 140 is formed on the tap part 110. When the reagent vessel 10 is inserted into the measuring cassette 20 (see FIG. 1), the tap part 110 is folded and then caught in the catching slot 142 corresponding to the tap part 110. Accordingly, it is possible to fix the tap part 110 without any shaking when the tap part 110 is folded.

Figure 8:
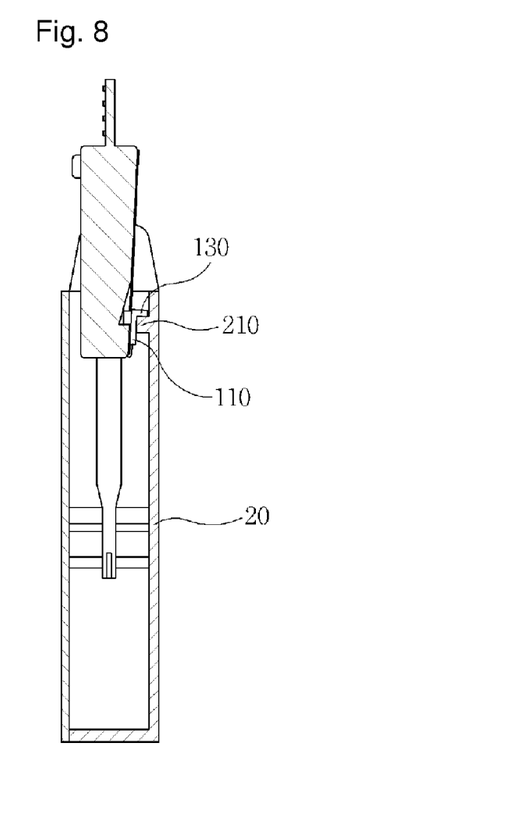
FIGS. 8 and 9 are views for explaining operations when the reagent vessel illustrated in FIG. 2 is inserted into a measuring cassette.
Figure 9:
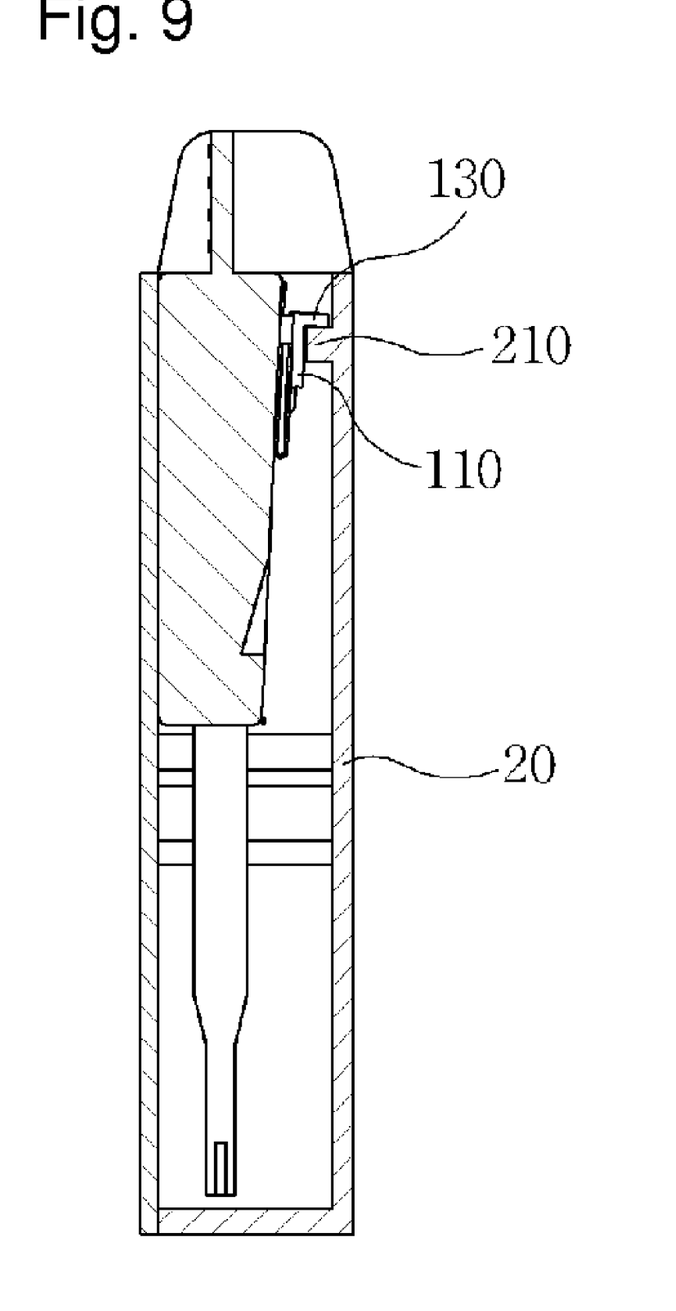

Meanwhile, FIGS. 8 and 9 are views for explaining operations when the reagent vessel 10 illustrated in FIG. 2 is inserted into the measuring cassette 20 (see FIG. 1).

Referring to FIG. 8, when the reagent vessel 10 is inserted into the measuring cassette 20, the tap part 110 is folded, and the catching member 130 of the reagent vessel 10 is caught in the reagent vessel catching jar 210 of the measuring cassette 20.

If the reagent vessel 10 is completely inserted into the measuring cassette 20, as shown in FIG. 9, the tap part 110 caught in the reagent vessel catching jar 210 is cut off and the adhesive cover (120 in FIG. 6) sealing up the reagent storage unit 100 is stripped off. The adhesive cover 120 may be stripped off to the degree of sufficiently discharging at least one reagent contained in the reagent storage unit 100. Also, at least one side of the reagent vessel 10 may incline downward in order to easily drop the reagent down. Furthermore, if the adhesive cover 120 is stripped off to a predetermined degree, the cassette catching jar 170 of the reagent vessel 10 is caught in the measuring cassette 20 so that the reagent vessel 10 is no longer inserted into the measuring cassette 20.

In summary, as illustrated in FIGS. 8 and 9, the adhesive cover 120 of the reagent vessel 10 is automatically stripped off to move a reagent into the measuring cassette 20 when the reagent vessel 10 is inserted into the measuring cassette 20. Accordingly, a measurer can control at least one reagent to be poured simultaneously and automatically to the measuring cassette 20 only by inserting the reagent vessel 10 into the measuring cassette 20.

While this invention has been particularly shown and described with reference to preferred embodiments thereof, it will be understood by those skilled in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

INDUSTRIAL APPLICABILITY

As described above, the present invention is applied to medical or environmental fields, such as medical diagnosis, medical treatment through medicine, and detection of harmful chemical materials.

The invention claimed is:

1. A reagent vessel to be inserted into a measuring cassette for measuring a biological sample, the reagent vessel comprising:
a reagent storage unit comprising at least one space storing a reagent to react with the biological sample; and
an adhesive cover configured to seal up the at least one space storing the reagent, and configured to be stripped off to discharge the reagent from the at least one space without any direct hand contact when the reagent vessel is inserted into the measuring cassette.

2. The reagent vessel of claim 1, further comprising a tap part formed in an edge of the reagent storage unit, and cut off by the measuring cassette when the reagent vessel is inserted into the measuring cassette, wherein the adhesive cover is stripped off by the tap part cut off when the reagent vessel is inserted into the measuring cassette, thereby discharging the reagent.

3. The reagent vessel of claim 2, further comprising a catching member through which the tap part folded by the measuring cassette when the reagent vessel is inserted into the measuring cassette is caught in the measuring cassette.

4. The reagent vessel of claim 2, further comprising:
a tap projection formed on the tap part; and
a catching slot on the reagent storage unit in which the tap projection is caught when the reagent vessel is inserted into the measuring cassette to fold the tap part.

5. The reagent vessel of claim 1, further comprising a handle.

6. The reagent vessel of claim 1, further comprising a sample injecting unit for injecting the biological sample into the reagent vessel.

7. The reagent vessel of claim 2, further comprising a cutting unit formed between the reagent storage unit and the tap part and having a plurality of slots.

8. The reagent vessel of claim 1, wherein at least one side of the reagent vessel inclines downward.

9. The reagent vessel of claim 1, wherein the at least one space is partitioned into a plurality of spaces so that different reagents are stored separately in the plurality of spaces.

10. The reagent vessel of claim 6, wherein the sample injecting unit is located below the reagent storage unit.

* * * * *